United States Patent
Carter et al.

(10) Patent No.: US 6,683,089 B2
(45) Date of Patent: Jan. 27, 2004

(54) N-ALLYOXYETHYL-1,2,3,4,5,6-HEXAHYDRO-2,6-METHANO-3-BENZAZOCINE-10-OLS

(75) Inventors: Adrian Carter, Bingen (DE); Helmut Ensinger, Ingelheim am Rhein (DE); Matthias Grauert, Biberach (DE); Detlef Andre Stiller, Biederitz (DE); Thomas Weiser, Wiesbaden (DE)

(73) Assignee: Boehringer Ingelheim Pharma GmbH & Co. KG, Ingelheim (DE)

( * ) Notice: Subject to any disclaimer, the term of this patent is extended or adjusted under 35 U.S.C. 154(b) by 0 days.

(21) Appl. No.: 10/354,516

(22) Filed: Jan. 30, 2003

(65) Prior Publication Data

US 2003/0162804 A1 Aug. 28, 2003

Related U.S. Application Data

(60) Provisional application No. 60/367,969, filed on Mar. 27, 2002.

(30) Foreign Application Priority Data

Feb. 2, 2002 (DE) .......................................... 102 04 276

(51) Int. Cl.[7] .............................................. A61K 31/349
(52) U.S. Cl. ......................................... 514/295; 546/97
(58) Field of Search ............................. 514/295; 546/97

(56) References Cited

U.S. PATENT DOCUMENTS

| 5,279,117 A | 1/1994 | Kaiser |
| 5,607,941 A | 3/1997 | Merz et al. |
| 5,731,318 A | 3/1998 | Carter et al. |
| 6,245,777 B1 | 6/2001 | Grauert et al. |
| 6,355,652 B1 | 3/2002 | Grauert et al. |
| 6,455,538 B1 | 9/2002 | Grauert et al. |

FOREIGN PATENT DOCUMENTS

| DE | 199 07 874 A1 | 8/2000 |
| DE | 199 57 156 A1 | 5/2001 |
| EP | 0 521 411 A1 | 1/1993 |

OTHER PUBLICATIONS

Trube, G. et al; "Dextromethorphan: Cellular Effects Reducing Neuronal Hyperactivity"; Epilepsia, 35 (Supp 5), 1994, pp. 562–567.

*Primary Examiner*—Amelin Owens
(74) *Attorney, Agent, or Firm*—Robert P. Raymond; Philip I. Datlow; Alan R. Stempel

(57) ABSTRACT

The present invention relates to 1,2,3,4,5,6-hexahydro-2,6-methano-3-benzazocin-10-ols of general formula 1

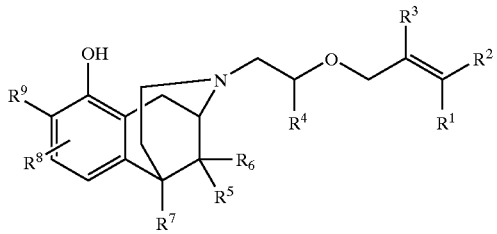

wherein the groups $R^1$, $R^2$, $R^3$, $R^4$, $R^5$, $R^6$, $R^7$, $R^8$ and $R^9$ have the meanings as set forth herein, processes for preparing them, pharmaceutical compositions thereof and their use in treating or preventing a disease or disorder by blocking the voltage-dependent sodium channel.

10 Claims, No Drawings

N-ALLYOXYETHYL-1,2,3,4,5,6-HEXAHYDRO-2,6-METHANO-3-BENZAZOCINE-10-OLS

RELATED APPLICATIONS

Benefit of U.S. Provisional Application Serial No. 60/367,969, filed on Mar. 27, 2002 is hereby claimed, and said application is herein incorporated by reference in its entirety.

DETAILED DESCRIPTION OF THE INVENTION

The present invention relates to substituted N-allyloxyethyl-1,2,3,4,5,6-hexahydro-2,6-methano-3-benzazocin-10-ols of general formula 1

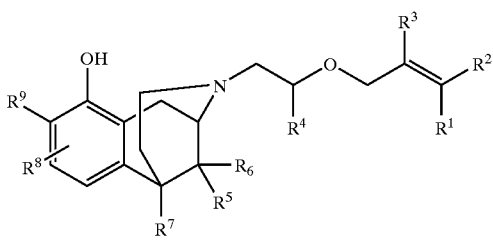

wherein
- $R^1$, $R^2$ and $R^3$ which may be identical or different, may denote hydrogen, methyl or ethyl;
- $R^4$ may denote hydrogen, methyl or ethyl;
- $R^5$, $R^6$ and $R^7$ which may be identical or different, may denote hydrogen, methyl or ethyl;
- $R^8$ and $R^9$ which may be identical or different, may denote hydrogen, fluorine, chlorine, bromine, methyl, ethyl, hydroxy or methoxy, optionally in the form of the racemates, the enantiomers, the diastereomers and the mixtures thereof, or the pharmacologically acceptable acid addition salts thereof.

Preferred compounds of general formula 1 are those wherein
- $R^1$, $R^2$ and $R^3$ which may be identical or different, may denote hydrogen or methyl;
- $R^4$ may denote hydrogen or methyl;
- $R^5$, $R^6$ and $R^7$ which may be identical or different, may denote hydrogen or methyl, preferably methyl;
- $R^8$ may denote hydrogen, methyl, hydroxy or methoxy, preferably hydrogen or methyl,
- $R^9$ may denote hydrogen or methyl, optionally in the form of the racemates, the enantiomers, the diastereomers and the mixtures thereof, as well as optionally the pharmacologically acceptable acid addition salts thereof.

Particularly preferred are the compounds of general formula 1 wherein
- $R^1$, $R^2$ and $R^3$ which may be identical or different, may denote hydrogen or methyl;
- $R^4$ may denote hydrogen or methyl;
- $R^5$, $R^6$ and $R^7$ may denote methyl;
- $R^8$ may denote hydrogen or methyl, preferably hydrogen;
- $R^9$ may denote hydrogen or methyl, optionally in the form of the racemates, the enantiomers, the diastereomers and the mixtures thereof, as well as optionally the pharmacologically acceptable acid addition salts thereof.

Of exceptional importance according to the invention are those compounds of general formula 1 which are in the 1R configuration and, if $R^4$ does not denote hydrogen, in the 2"S configuration. These stereoisomers which are preferred according to the invention may also be represented by general formula 1'

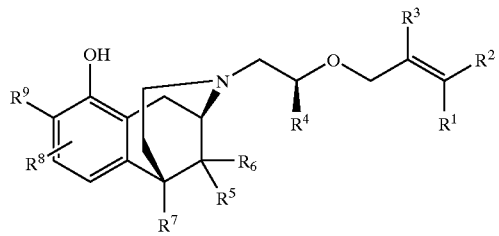

wherein the groups $R^1$, $R^2$, $R^3$, $R^4$, $R^5$, $R^6$, $R^7$, $R^8$ and $R^9$ may have the meanings given above.

Of particular interest are the following compounds of general formula 1:
- (2R)-N-allyloxyethyl-1,2,3,4,5,6-hexahydro-6,11,11-trimethyl-2,6-methano-3-benzazocin-10-ol-hydrochloride;
- (2R,2"S)-N-(2-allyloxy-propyl)-1,2,3,4,5,6-hexahydro-6,11,11-trimethyl-2,6-methano-3-benzazocin-10-ol-hydrochloride.

If desired, the compounds of general formula (1) may be converted into the salts thereof, particularly, for pharmaceutical use, into the pharmacologically acceptable acid addition salts thereof with an inorganic or organic acid. Examples of acids for this purpose include for example succinic acid, hydrobromic acid, acetic acid, fumaric acid, maleic acid, methanesulphonic acid, lactic acid, phosphoric acid, hydrochloric acid, sulphuric acid, tartaric acid or citric acid. Moreover, mixtures of these acids may also be used. The compounds claimed are blockers of the voltage-dependent sodium channel. These are compounds which displace batrachotoxin (BTX) with a high affinity ($K_1$<500 nM) competitively or non-competitively from the binding site on the sodium channel. Such substances exhibit "use-dependency" while the sodium channels are blocked, i.e. in order to bind the substances at the sodium channel, the sodium channels first have to be activated. Maximum blockage of the sodium channels is only achieved after repeated stimulation of the sodium channels. Consequently, the substances bind preferentially to sodium channels which are activated a number of times. As a result, the substances are in a position to become effective particularly in those parts of the body which are pathologically overstimulated. The compounds of general formula 1 according to the invention can thus be used to treat diseases which are caused by a functional disorder resulting from overstimulation. These include diseases such as arrhythmias, spasms, cardiac and cerebral ischaemias, pain and neurodegenerative diseases of various origins. These include, for example: epilepsy, hypoglycaemia, hypoxia, anoxia, brain trauma, brain oedema, cerebral stroke, perinatal asphyxia, degeneration of the cerebellum, amyotropic lateral sclerosis, Huntington's disease, Alzheimer's disease, Parkinson's disease, cyclophrenia, hypotonia, cardiac infarction, heart rhythm disorders, angina pectoris, chronic pain, neuropathic pain and local anaesthesia.

Consequently, in another aspect, the invention relates to the use of compounds of general formula 1 as pharmaceutical compositions, particularly as pharmaceutical compositions wherein the blocking of the voltage-dependent sodium channel may have a therapeutic benefit.

Preferably, the compounds of general formula 1 are used according to the invention to prepare a pharmaceutical composition for the prevention or treatment of arrhythmias, spasms, cardiac and cerebral ischaemias, pain and neurodegenerative diseases.

Most preferably, the compounds of general formula 1 are used as described above according to the invention to prepare a pharmaceutical composition for the prevention or treatment of epilepsy, hypoglycaemia, hypoxia, anoxia, brain trauma, brain oedema, cerebral stroke, perinatal asphyxia, degeneration of the cerebellum, amyotropic lateral sclerosis, Huntington's disease, Alzheimer's disease, Parkinson's disease, cyclophrenia, hypotonia, cardiac infarction, heart rhythm disorders, angina pectoris, chronic pain, neuropathic pain and local anaesthesia.

The blocking action on the sodium channel may be demonstrated by the test system which tests the BTX binding to the sodium channel [S. W. Postma & W. A. Catterall, Mol. Pharmacol 25, 219–227 (1984)] as well as by patch-clamp experiments which show that the compounds according to the invention block the electrically stimulated sodium channel in a "use-dependent" manner [W. A. Catterall, Trends Pharmacol. Sci., 8, 57–65 (1987)]. By a suitable choice of cell system (e.g. neuronal, cardiac, DRG cells) it is possible to test the effect of the substances on different subtypes of sodium channel.

The sodium channel blocking property of the compounds according to the invention can be demonstrated by the blocking of the veratridine-induced release of glutamate [S. Villanueva, P. Frenz, Y. Dragnic, F. Orrego, Brain Res. 461, 377–380 (1988)]. Veratridine is a toxin which opens the sodium channel permanently. This leads to an increased influx of sodium ions into the cell. This sodium influx leads to an increased release of glutamate in the neuronal tissue. The compounds according to the invention antagonise this release of glutamate.

Neuroprotective properties were demonstrated by a protective effect in a rat MCAO model [U. Pschorn & A. J. Carter, J. Stroke Cerebrovascular Diseases, 6, 93–99 (1996)] and a malonate-induced lesion model [M. F. Beal, Annals of Neurology, 38, 357–366 (1995) and J. B. Schulz, R. T. Matthews, D. R. Henshaw and M. F. Beal, Neuroscience, 71, 1043–1048 (1996)].

Analgesic effects can be investigated in-models of diabetic neuropathy and in a ligature model [C. Courteix, M. Bardin, C. Chantelauze, J. Lavarenne, A. Eschalier, Pain 57, 153–160 (1994); C. Courteix, A. Eschalier, J. Lavarenne, Pain 53, 81–88 (1993); G. J. Bennett and Y. -K. Xie, Pain 33, 87–107 (1988)].

It has also been reported that sodium channel blockers can be used to treat cyclophrenia (manic depressive disorder) [J. R. Calabrese, C. Bowden, M. J. Woyshville; in: Psychopharmacology: The Fourth Generation of Progress (Eds.: D. E. Bloom and D. J. Kupfer) 1099–1111. New York: Raven Press Ltd.].

The compounds 1 according to the invention may be prepared analogously to methods of synthesis known per se. One possible method of synthesis is shown in Diagram 1. The 1,2,3,4,5,6-hexahydro-2,6-methano-3-benzazocin-10-ols (2) shown as starting compounds in Diagram 1 may be obtained by methods of synthesis known in the art. In this respect reference is hereby made to European Patent Application EP-A-52 1422 and to International Patent Applications WO 97/06146 and WO 99/14199.

Diagram 1:

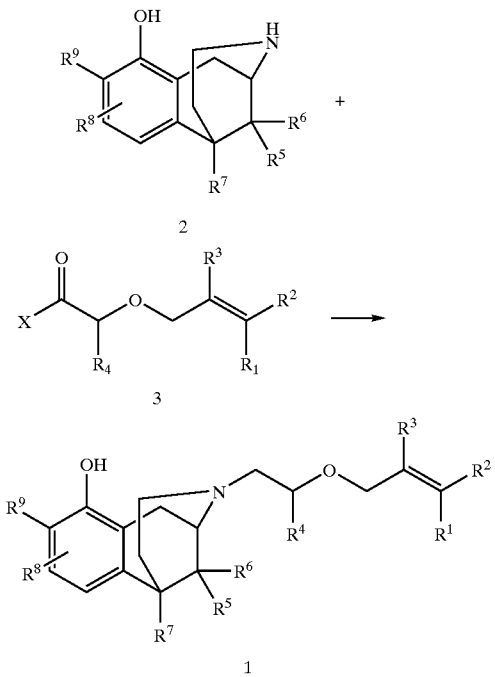

The synthesis component 3 contains a leaving group X, which is preferably chlorine, bromine, hydroxy or a methoxy or ethoxy group. For a detailed explanation of the synthesis of the compounds of formula 1 according to the invention reference is made to the experimental procedures described below. One possible method of obtaining compounds of formula 1 wherein $R^9$ denotes methyl is shown in Diagram 2.

Diagram 2:

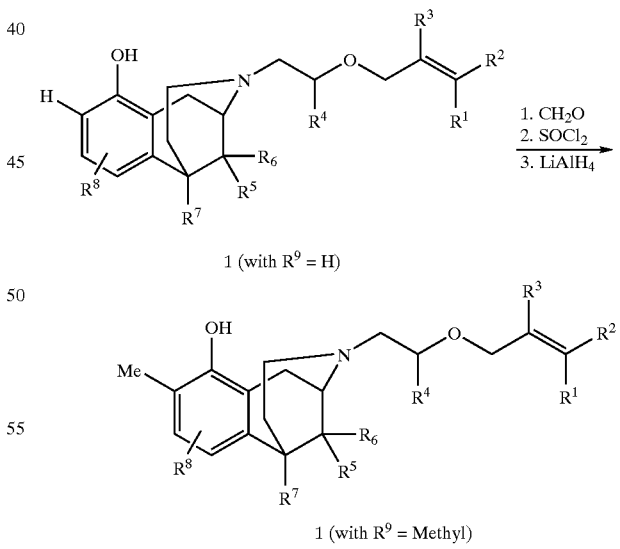

For a detailed explanation of the synthesis of the compounds of formula 1 according to the invention as shown in Diagram 2 reference is again made to the experimental procedures described below.

The Examples that follow serve to illustrate the invention more fully without restricting it to the compounds and processes disclosed by way of example.

EXAMPLE 1

(2R)-N-allyloxyethyl-1,2,3,4,5,6-hexahydro-6,11,11-trimethyl-2,6-methano-3-benzazocin-10-ol-hydrochloride

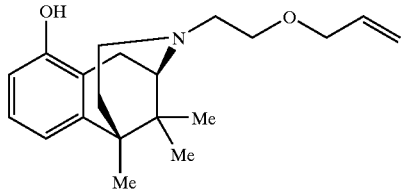

1.8 g of allyloxyacetic acid are placed in 15 mL dichloromethane, combined with 4.8 g of TBTU and 7.5 mL of ethyldiisopropylamine and stirred for 15 min. at RT. Then the mixture is cooled to −5° C. and 3.1 g of 1,2,3,4,5,6-hexahydro-6,11,11-trimethyl-2,6-methano-3-benzazocin-10-ol are added. The mixture is stirred for 30 min at 0° C., and for 1 h at RT. Then it is washed once with 100 ml of 2N HCL and 100ml of 10% potassium carbonate solution, dried and evaporated down in vacuo. The residue is taken up in 50 mL of THF and added dropwise under nitrogen to a suspension of 1.0 g of lithium aluminium hydride in 50 ml of THF (temp. increases to 35° C.). Then the mixture is heated to 50° C., stirred for 1 h, cooled and 1 ml of water is added dropwise at 0–10° C., the mixture is stirred for 30 min, 3 ml of NaOH are added and the mixture is stirred for another 30 min. The precipitate is suction filtered, the mother liquor is evaporated down in vacuo and the residue is filtered through a short column (about 75 ml of silica gel; dichloromethane 70, ethyl acetate 20, methanol 10). The appropriate fractions are evaporated down in vacuo, and crystallised from acetone+eth. HCl. Yield 2.8 g (77%), melting point: 236° C.; $[\alpha]_D^{20}=-78,3°$ (c=1; methanol).

EXAMPLE 2

(2R,2"S)-N-(2-allyloxy-propyl)-1,2,3,4,5,6-hexahydro-6,11,11-trimethyl-2,6-methano-3-benzazocin-10-ol-hydrochloride

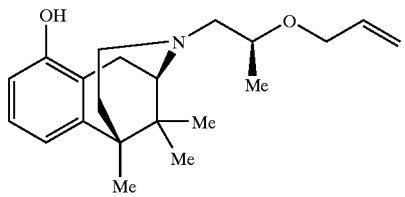

This is prepared analogously to the method according to Example 1.

Yield 56%, melting point: 239° C.; $[\alpha]_D^{20}=-33.9°$ (c=1; methanol).

EXAMPLE 3

(2R,2"S)-N-(2-but-2-enoxy-propyl)-1,2,3,4,5,6-hexahydro-6,11,11-trimethyl-2,6-methano-3-benzazocin-10-ol-hydrochloride

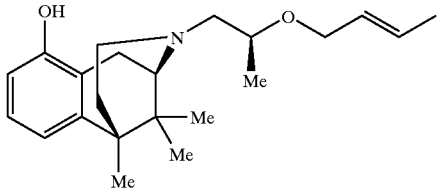

This is prepared analogously to the method according to Example 1.

Yield 47%, melting point: 205° C.

EXAMPLE 4

(2R,2"S)-N-[2-(2-methyl-propenoxy)-propyl]-1,2,3.4,5.6-hexahydro-6,11,11-trimethyl-2,6-methano-3-benzazocin-10-ol-hydrochloride

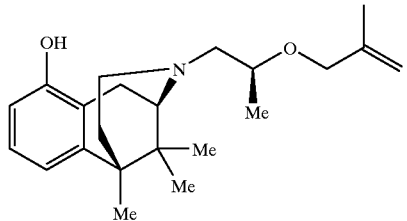

This is prepared analogously to the method according to Example 1.

Yield 12%, melting point: 240° C.; $[\alpha]_D^{20}=-29.6°$ (c=1; methanol).

EXAMPLE 5

(2R)-N-[2-allyloxyethyl]-1,2,3,4,5,6-hexahydro-6,9,11,11-tetramethyl-2,6-methano-3-benzazocin-10-ol-hydrochloride

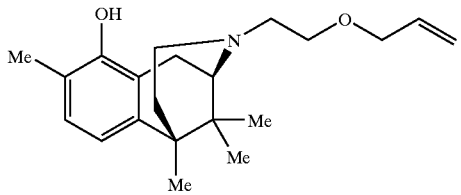

1.9 g of (2R)-N-allyloxyethyl-1,2,3,4,5,6-hexahydro-6,11,11-trimethyl-2,6-methano-3-benzazocin-10-ol-hydrochloride (Example 1) are dissolved in 40 mL methanol and combined with 3 g of 30% formal in solution and 3 mL of 4 N NaOH. The mixture is heated to 50° C. for 12 hours, the solvent is eliminated in vacuo, the residue is combined with 100 mL of water and extracted twice with 200 ml of ether. The organic phase is washed with water, dried and evaporated down in vacuo. The residue is dissolved in 20 mL of dichloromethane and 1.5 g of $SOCl_2$ are added dropwise at RT. After 30 min. the mixture is evaporated down in vacuo, the residue is taken up in 20 ml of THF and added dropwise under nitrogen to a suspension of 0.5 g of lithium aluminium hydride in 20 ml of tetrahydrofuran. Then it is heated to 50° C. for 2 h, cooled, 1.5 mL of 4N NaOH are added dropwise and the resulting mixture is stirred for 30 min. The precipitate is suction filtered and the mother liquor evaporated down in vacuo. The residue is filtered through a short silica gel column (about 30 mL of silica gel, about 250 mL of ethyl acetate). The appropriate fractions are evaporated down in vacuo and crystallised from acetone+eth. HCl.

Yield 1.1 g (56%), melting point: 212° C., $[\alpha]_D^{20}=-71.6°$ (c=1; methanol).

EXAMPLE 6

(2R,2"S)-N-[2-allyloxy-propyl]-1,2,3.4,5,6-hexahydro-6,9,11,11-tetramethyl-2,6-methano-3-benzazocin-10-ol-hydrochloride

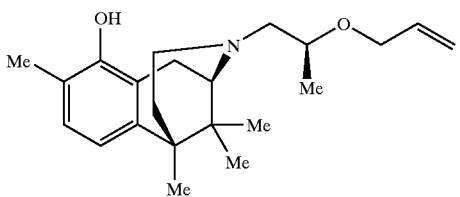

This is prepared analogously to the method according to Example 5, starting from Example 2.

Yield 60%, melting point: 215° C.; $[\alpha]_D^{20}=-29.30$ (c=1; methanol).

The compounds according to the invention may be administered orally, transdermally, by inhalation or parenterally. The compounds according to the invention occur as active ingredients in conventional preparations, for example in compositions which consist essentially of an inert pharmaceutical carrier and an effective dose of the active substance, such as for example tablets, coated tablets, capsules, lozenges, powders, solutions, suspensions, emulsions, syrups, suppositories, transdermal systems etc. An effective dose of the compounds according to the invention is between 1 and 1000, preferably between 1 and 500, most preferably between 5–300 mg/dose for oral administration, and between 0.00 1 and 50, preferably between 0. 1 and 10 mg/dose for intravenous, subcutaneous or intramuscular administration. For inhalation, according to the invention, solutions containing 0.01 to 1.0, preferably 0.1 to 0.5% active substance are suitable. For administration by inhalation the use of powders is preferred. By virtue of their particular physico-chemical properties it is also possible to use the compounds according to the invention as a solution for infusion, preferably in a physiological saline or nutrient saline solution. In an infusion, 10–100 mg/h, preferably 25–60 mg/h might be administered. This latter method of administration is of exceptional importance according to the invention.

The compounds according to the invention may be used on their own or in conjunction with other active substances according to the invention, optionally also in conjunction with other pharmacologically active substances. Suitable preparations include for example tablets, capsules, suppositories, solutions, elixirs, emulsions or dispersible powders. Suitable tablets may be obtained, for example, by mixing the active substance(s) with known excipients, for example inert diluents such as calcium carbonate, calcium phosphate or lactose, disintegrants such as corn starch or alginic acid, binders such as starch or gelatine, lubricants such as magnesium stearate or talc and/or agents for delaying release, such as carboxymethyl cellulose, cellulose acetate phthalate, or polyvinyl acetate. The tablets may also comprise several layers.

Coated tablets may be prepared accordingly by coating cores produced analogously to the tablets with substances normally used for tablet coatings, for example collidone or shellac, gum arabic, talc, titanium dioxide or sugar. To achieve delayed release or prevent incompatibilities the core may also consist of a number of layers. Similarly the tablet coating may consist of a number of layers to achieve delayed release, possibly using the excipients mentioned above for the tablets.

Syrups or elixirs containing the active substances or combinations thereof according to the invention may additionally contain a sweetener such as saccharine, cyclamate, glycerol or sugar and a flavour enhancer, e.g. a flavouring such as vanillin or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Solutions for injection are prepared in the usual way, e.g. with the addition of preservatives such as p-hydroxybenzoates, or stabilisers such as alkali metal salts of ethylenediamine tetraacetic acid, and transferred into injection vials or ampoules.

Capsules containing one or more active substances or combinations of active substances may for example be prepared by mixing the active substances with inert carriers such as lactose or sorbitol and packing them into gelatine capsules.

Suitable suppositories may be made for example by mixing with carriers provided for this purpose, such as neutral fats or polyethyleneglycol or the derivatives thereof.

A therapeutically effective daily dose is between 1 and 2500 mg, preferably 10 to 1000 mg per adult.

The Examples which follow illustrate the present invention without restricting its scope:

EXAMPLES OF PHARMACEUTICAL FORMULATIONS

| A) | Tablets | per tablet |
|---|---|---|
| | active substance | 100 mg |
| | lactose | 140 mg |
| | corn starch | 240 mg |
| | polyvinylpyrrolidone | 15 mg |
| | magnesium stearate | 5 mg |
| | | 500 mg |

The finely ground active substance, lactose and some of the corn starch are mixed together. The mixture is screened, then moistened with a solution of polyvinylpyrrolidone in water, kneaded, wet-granulated and dried. The granules, the remaining corn starch and the magnesium stearate are screened and mixed together. The mixture is compressed to produce tablets of suitable shape and size.

| B) | Tablets | per tablet |
|---|---|---|
| | active substance | 80 mg |
| | corn starch | 190 mg |
| | lactose | 55 mg |
| | microcrystalline cellulose | 35 mg |
| | polyvinylpyrrolidone | 15 mg |
| | sodium-carboxymethyl starch | 23 mg |
| | magnesium stearate | 2 mg |
| | | 400 mg |

The finely ground active substance, some of the corn starch, lactose, microcrystalline cellulose and polyvinylpyrrolidone are mixed together, the mixture is screened and worked with the remaining corn starch and water to form a granulate which is dried and screened. The sodium-carboxymethyl starch and the magnesium stearate are added and mixed in and the mixture is compressed to form tablets of a suitable size.

| C) | Coated tablets | per coated tablet |
|---|---|---|
| | Active substance | 5 mg |
| | Corn starch | 41.5 mg |
| | Lactose | 30 mg |
| | Polyvinylpyrrolidone | 3 mg |
| | Magnesium stearate | 0.5 mg |
| | | 80 mg |

The active substance, corn starch, lactose and polyvinylpyrrolidone are thoroughly mixed and moistened with water. The moist mass is pushed through a screen with a 1 mm mesh size, dried at about 45° C. and the granules are then passed through the same screen. After the magnesium stearate has been mixed in, convex tablet cores with a diameter of 6 mm are compressed in a tablet-making machine . The tablet cores thus produced are coated in known manner with a covering consisting essentially of sugar and talc. The finished coated tablets are polished with wax.

| D) | Capsules | per capsule |
|---|---|---|
| | Active substance | 50 mg |
| | Corn starch | 268.5 mg |
| | Magnesium stearate | 1.5 mg |
| | | 320 mg |

The substance and corn starch are mixed and moistened with water. The moist mass is screened and dried. The dry granules are screened and mixed with magnesium stearate. The finished mixture is packed into size 1 hard gelatine capsules.

| E) | Ampoule solution | |
|---|---|---|
| | active substance | 50 mg |
| | sodium chloride | 50 mg |
| | water for inj. | 5 ml |

The active substance is dissolved in water at its own pH or optionally at pH 5.5 to 6.5 and sodium chloride is added to make it isotonic. The solution obtained is filtered free from pyrogens and the filtrate is transferred under aseptic conditions into ampoules which are then sterilised and sealed by fusion. The ampoules contain 5 mg, 25 mg and 50 mg of active substance.

| F) | Suppositories | |
|---|---|---|
| | Active substance | 50 mg |
| | Solid fat | 1650 mg |
| | | 1700 mg |

The hard fat is melted. At 40° C. the ground active substance is homogeneously dispersed. It is cooled to 38° C. and poured into slightly chilled suppository moulds.

We claim:

1. A compound of formula 1

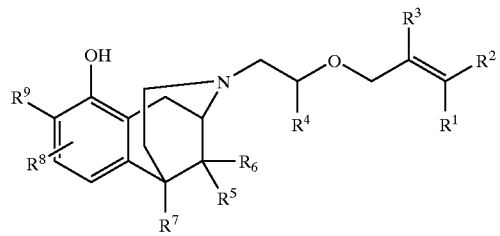

wherein
   $R^1$, $R^2$ and $R^3$ which may be identical or different, may each denote hydrogen, methyl or ethyl;
   $R^4$ is hydrogen, methyl or ethyl;
   $R^5$, $R^6$ and $R^7$ which may be identical or different, may each denote hydrogen, methyl or ethyl;
   $R^8$ and $R^9$ which may be identical or different, may each denote hydrogen, fluorine, chlorine, bromine, methyl, ethyl, hydroxy or methoxy,
optionally in the form of a racemate, an enantiomer, a diastereomer or mixture thereof, or a pharmacologically acceptable acid addition salt thereof.

2. A compound of formula 1 according to claim 1, wherein
   $R^1$, $R^2$ and $R^3$ which may be identical or different, may each denote hydrogen or methyl;
   $R^4$ is hydrogen or methyl;
   $R^5$, $R^6$ and $R^7$ which may be identical or different, may each denote hydrogen or methyl;
   $R^8$ is hydrogen, methyl, hydroxy or methoxy,
   $R^9$ is hydrogen or methyl,
optionally in the form of a racemate, an enantiomer, a diastereomer or mixture thereof, or a pharmacologically acceptable acid addition salt thereof.

3. A compound of formula 1 according to claim 1, wherein
- $R^1$, $R^2$ and $R^3$ which may be identical or different, may each denote hydrogen or methyl;
- $R^4$ is hydrogen or methyl;
- $R^5$, $R^6$ and $R^7$ are each methyl;
- $R^8$ is hydrogen or methyl;
- $R^9$ is hydrogen or methyl, optionally in the form of a racemate, an enantiomer, a diastereomer or mixture thereof, or a pharmacologically acceptable acid addition salt thereof.

4. A compound of formula 1 according to claim 1, wherein
- $R^1$, $R^2$ and $R^3$ which may be identical or different, may each denote hydrogen or methyl;
- $R^4$ is hydrogen or methyl;
- $R^5$, $R^6$ and $R^7$ are each methyl;
- $R^8$ is hydrogen;
- $R^9$ is hydrogen or methyl, optionally in the form of a racemate, an enantiomer, a diastereomer or mixture thereof, or a pharmacologically acceptable acid addition salt thereof.

5. A compound of formula 1 according to claim 1, wherein said compound is in the 1R configuration and also, if $R^4$ is not hydrogen, in the 2"S configuration.

6. A pharmaceutical composition comprising a compound of formula 1 according to claim 1 and one or more excipients or carriers.

7. A method of blocking the voltage-dependent sodium channel in a patient comprising administering to said patient a compound of formula 1 according to claim 1.

8. A method of treating a disease or disorder by blocking the voltage-dependent sodium channel in a patient comprising administering to said patient a therapeutically effective amount compound of formula 1 according to claim 1.

9. A method of treating an arrhythmia, spasm, cardiac or cerebral ischaemia, pain or neurodegenerative disease in a patient comprising administering to said patient a therapeutically effective amount compound of formula 1 according to claim 1.

10. A method of treating epilepsy, hypoglycaemia, hypoxia, anoxia, brain trauma, brain oedema, cerebral stroke, perinatal asphyxia, degeneration of the cerebellum, amyotropic lateral sclerosis, Huntington's disease, Alzheimer's disease, Parkinson's disease, cyclophrenia, hypotonia, cardiac infarction, a heart rhythm disorder, angina pectoris, chronic pain, neuropathic pain or local anaesthesia in a patient comprising administering to said patient a therapeutically effective amount compound of formula 1 according to claim 1.

* * * * *